(12) United States Patent
Welch et al.

(10) Patent No.: US 8,226,776 B1
(45) Date of Patent: Jul. 24, 2012

(54) TREATING PROTEIN-CONTAINING LIQUIDS

(75) Inventors: Anne Gillian Welch, Fife (GB); Peter Reynolds Foster, Edinburgh (GB)

(73) Assignee: Bio Products Laboratory Limited (GB)

( * ) Notice: Subject to any disclaimer, the term of this patent is extended or adjusted under 35 U.S.C. 154(b) by 0 days.

(21) Appl. No.: 09/889,645

(22) PCT Filed: Jan. 19, 2000

(86) PCT No.: PCT/GB00/00123
§ 371 (c)(1),
(2), (4) Date: Jan. 24, 2002

(87) PCT Pub. No.: WO00/43048
PCT Pub. Date: Jul. 27, 2000

(30) Foreign Application Priority Data

Jan. 19, 1999 (GB) .................................. 9901139.7
May 7, 1999 (GB) .................................. 9910476.2

(51) Int. Cl.
*G01N 33/53* (2006.01)
*G01N 33/68* (2006.01)

(52) U.S. Cl. ............ 134/42; 424/204.1; 422/37; 422/28

(58) Field of Classification Search ................ 428/313.7; 435/4; 524/9, 448; 528/482; 505/820
See application file for complete search history.

(56) References Cited

U.S. PATENT DOCUMENTS

| | | |
|---|---|---|
| 4,278,551 A | 7/1981 | Hou et al. |
| 4,288,462 A | 9/1981 | Hou et al. |
| 4,309,247 A | 1/1982 | Hou et al. |
| 5,696,236 A | 12/1997 | Omar et al. |
| 6,083,408 A * | 7/2000 | Breitenbach et al. ......... 210/753 |
| 6,407,212 B1 * | 6/2002 | Morgenthaler et al. ....... 530/380 |
| 6,627,088 B1 | 9/2003 | Breitenbach et al. |

FOREIGN PATENT DOCUMENTS

| | | |
|---|---|---|
| AU | 742239 | 8/1999 |
| DE | EP2910289 A1 | 9/1990 |
| EP | 0798003 A2 | 10/1997 |
| EP | 0 937 735 B1 | 2/2003 |
| GB | 2 045 828 A * | 11/1980 |
| GB | 2045828 A | 11/1980 |
| IL | 59339 A | 9/1982 |
| IL | XP-002135499 | 9/1982 |
| WO | WO 96/05846 | 2/1996 |
| WO | WO 00/43048 | 7/2000 |

OTHER PUBLICATIONS

Barnard et al. The measurement of prion protein in bovine brain tissue using differential extraction and DELFIA as a diagnostic test for BSE. Luminescence (2000) vol. 15, No. 6, pp. 357-362.*

Bennion et al. Protein conformation and diagnostic tests: the prion protein. Clinical Chemistry (2002) vol. 48, No. 12, pp. 2105-2114.*

(Continued)

*Primary Examiner* — Agnieszka Boesen
(74) *Attorney, Agent, or Firm* — Myers Bigel Sibley & Sajovec, PA

(57) ABSTRACT

Abnormal infective prion proteins are removed from liquids containing biologically active substances, particularly blood products, by filtration using a depth filter formed of a matrix comprising solid particles of porous material and having a pore size less than 6 microns. Preferably the filter is free of cationic or anionic charged material.

43 Claims, No Drawings

OTHER PUBLICATIONS

Prusiner S. B., Measurement of the scrapie agent using an incubation time interval assay. Annals of Neurology (1982) vol. 11, No. 4, pp. 353-358.*

McLean et al. Scrapie infections initiated at varying doses: an analysis of 117 titration experiments. Philos Trans R Society London (2000) vol. 355, pp. 1043-1050.*

Taylor et al. Inactivation of the bovine spongiform encephalopathy agent by rendering procedures. Veterinary Record (1995), vol. 137, No. 24, pp. 605-610.*

Foster et al., Assesment of the potential of plasma fractionation prosesses to remove causative agents of transmissible spongiform encephalopathy. 1999. Transfusion Medicine. vol. 9, p. 3-14.*

Encyclopedia Britannica, diatomaceous earth, www.britanica.com/eb/article-9030299/diatomaceous-earth.*

Gerba et al. (Applied and Environmental Microbiology, 1985, p. 1375-1377).*

Brown et al. (Transfusion, 1998, vol. 38, p. 810-816).*

International Search Report, International Application No. PCT/GB00/00123;Jul. 27, 2000.

Foster,P.R., "Assessment of the Potential of Plasma Fractionation Processes to Remove Causative Agents of Transmissible Spongiform Encephalopathy", *Transfusion Medicine*, 9, 3-14.

Hou et al., "Capture of Latex Beads, Bacteria, Endotoxin, and Viruses by Charge-Modified Filters", *Applied and Environmental Microbiology*, pp. 892-896, Nov. 1980.

Gale et al., A Review "Development of a Risk Assessment for BSE in the Aquatic Environment", *Journal of Applied Microbiology*, 84, pp. 467-477, 1998.

Blum et al. "A Bovine Spongiform Encephalopathy Validation Study for Aprotinin and Bovine Serum Albumin," *BioPharm*, 28-34 (Apr. 1998).

Hunter, G.D. et al., "Studies on the Heat Stability and Chromatographic Behaviour of the Scrapie Agent," *J. Gen. Microbiol.* 37:251-258 (1964).

Millson, G.C. et al. "An Experimental Examination of the Scrapie Agent in Cell Membrane Mixtures," *J. Comp. Path.* 81:255-265 (1971).

EEC Regulatory Document, "Guidelines for Minimizing the Risk of Transmitting Agents Causing Spongiform Encephalopathy via Medicinal Products," *Biologicals* 20:155-158 (1992).

Reichl et al., "Studies on the removal of a bovine spongiform encephalopathy-derived agent by processes used in the manufacture of human immunoglobulin," *Vox Sanguinis*, 83:137-145 (2002).

Hou, K. et al. (1990). "Depyrogenation by Endotoxin Removal with Positively Charged Depth Filter Cartridge" *Journal of Parenteral Science & Technology*, 44(4):204-209.

Meltzer, T.H. et al. (1998) *Filtration in the Biopharmaceutical Industry*. Chapter 3, "Charge-Modified Filter Media" pp. 95-125; Chapter 10, "*Filtrative Particle Removal from Liquids*" pp. 259-266; Chapter 25, "Prefiltration Technology" pp. 783-789, Marcel Dekker, Inc.

Statement from Pall Corporation regarding the charge properties of the filter types KS80 and K200 P according to the invention, dated Feb. 25, 2005 (5 pages).

Flan et al. "Evaluation of TSE removal procedures in the manufacture of plasma products", *Who Consultation on Tissue Infectivity Distribution in TSEs* (29 pages) (2005).

Further statement from Pall Corporation regarding the charge properties of the filter types KS80 and K200 P according to the invention, dated Mar. 26, 2007.

EMEA document "CHMP Position Statement on Creutzfeldt-Jakob Disease and Plasma-Derived and Urine-Derived Medicinal Products" (17 pages) (2004).

Patel et al. "Creating lipid-free protein solutions", *Manufacturing Chemist* pp. 34-35 (1992).

Hou et al. "Lipid Removal from Protein Solution by Depth Filter", *Fluid/Particle Separation Journal*; pp. 108-110 (1998).

Patel "Charge Modified Depth Filter—Technology and its Evolution", *Filtration & Separation* pp. 221-226 (1992).

Brown et al. "Further studies of blood infectivity in an experimental model of transmissible spongiform encephalopathy, with an explanation of why blood components do not transmit Creutzfeldt-Jakob disease in humans", *Transfusion* 39:1169-1178. (1999).

Seitz Filtration K200 Quality Specification (3 pages) (1989).

Cuno Zeta Plus Filter Media (2 pages) (1999).

Notice of Opposition by ZLB Behring GmbH in European Patent No. 1144015 B1 (2005).

Appeal by CSL Behring GmbH in European Patent No, 1144015 B1 (2007).

Letter from Pall Corporation to CSL Behring dated Mar. 26, 2007.

Decision to maintain the European patent in amended form in European Patent No. 1144015 B1 dated Oct. 21, 2010.

* cited by examiner

TREATING PROTEIN-CONTAINING LIQUIDS

CROSS-REFERENCE TO RELATED APPLICATIONS

The present application is a U.S. national phase application of PCT International Application No. PCT/GB00/00123, having an international filing date of Jan. 19, 2000 and claiming priority to Great Britain Application Nos. 9901139.7 filed Jan. 19, 1999 and 9910476.2 filed May 7, 1999, the disclosures of which are incorporated herein by reference in their entirety. The above PCT International Application was published in the English language and has International Publication No. WO 00/43048.

The present invention relates to a method for the removal of abnormal infective prion proteins associated with transmissable spongiform encephalopathies (TSEs) from an aqueous liquid containing natural products, especially biologically active proteins. The invention also relates to proteins (including foodstuffs and biologically active proteins) and medicinal compositions therefrom where the infective prion has been removed or inactivated.

There is concern about the potential transmission of Jif TSEs such as Creutzfeldt-Jakob Disease (CJD) via whole blood or blood derived biopharmaceuticals. This concern has been heightened by a postulated link between bovine spongiform encephalopy (BSE) and a new variant form of CJD (vCJD) in humans. CJD is a progressive neurodegenerative disease caused by an unusual infectious agent that replicates in the lymphoreticular tissue and the central nervous system of its host. The nature of the agent is unresolved at present but two main hypotheses have been advanced. The first is the prion or infectious protein hypothesis; and the second is the virion hypothesis which encompasses a combination of host encoded protein with regulatory nucleic acid.

Medicinal compositions for intravenous infusion, intramuscular infusion and topical application have been prepared from human blood plasma for over four decades in a specialised but significant section of the pharmaceutical processing industry. A principal area of concern in the safety of these products has been potential contamination with blood born viruses. However, the development of screening methods together with technology for the inactivation or removal of potentially contaminating viruses has greatly improved the safety of blood and preparations derived therefrom.

There is currently considerable concern about the possibility that biopharmaceutical products from human or animal sources may transmit TSEs. Although the precise nature of the infective agent in TSEs is at present unclear, TSEs such as Scrapie in sheep and CJD or vCJD in humans are associated with abnormal prion related proteins (PrPs). Suitable screening mentions have not yet been developed for abnormal PrPs, which are also extremely resistant to physical and chemical means of inactivation. For example, the EEC regulatory document (CPM Guidelines for Minimising the Risk of Transmitting Agents causing Spongiform Encephalopathies by Medicinal Products: Biologicals, 20, pp 155-158, 1992) recommends autoclaving at about 130° C. for upto an hour, treatment with 1N sodium hydroxide for 1 hour or treatment with sodium hypochlorite for 1 hour. Such techniques are, however, quite unsuitable for the treatment of biologically active protein containing materials since they result in total inactivation of the protein.

There is therefore a need to develop methods of removal or inactivation of abnormal infective prion proteins from animal, or human derived medicinal or food products which are effective yet do not substantially degrade and/or remove the biological activity or food value of the product.

A major problem relates to the ill defined nature of the abnormal prion protein. The normal form of this protein is found in mammalian cells and is present in high levels in brain and lymphoreticular tissues. It is composed of highly membrane associated 33-35 KDa phosphoinositol glycoprotein, which is completely sensitive to digestion with proteinase K. The infectious (abnormal) form of the protein has been shown to exist in an altered conformational form, contains a high level of β pleated-sheet, and is resistant to digestion with proteinase K. The change in conformation is thought to result in the protein becoming highly insoluble, forming aggregates which then deposit in the infected tissue as fibrils or amyloid plaques. The unknown properties of the abnormal prion proteins, and particularly the state of aggregation makes the prediction of suitable removal or inactivation techniques very difficult.

In the prior art, removal or inactivation by chromatographic techniques has been attempted. Hunter and Milison (J. Gen. Microbiol., 1964, vol. 37 pp 251-258) showed examples of the chromatographic behaviour of scrapie-infected brain homogenate on DEAE cellulose adsorption and calcium phosphate columns. International patent application WO97/3454 relates to the removal of abnormal prion proteins from solutions of albumin or reagent grade animal serum using typically expensive mixed ion exchange and hydrophobic solid phases.

Blum et al (BioPharm. 11(4) pp 28-34, 1998) investigated the effectiveness of various steps (i.e. heating, precipitation, absorption with filter aid and ion-exchange chromatography) in the production of aprotinin and bovine serum albumin in removing added spikes of scrapie as a model source of TSE. However, it is unclear which of the above elements are essential or required in the removal of the scrapie agent.

Patent specification EP0798003 discloses filtration as rosF a way of removing unwanted contaminants. A positively charged depth filter of 0.25 to 2.0 micron pore size also carrying a cation resin, was used for the removal of viruses from biologically active protein solutions. Morgenthaler (TSE issues, Cambridge Health Tech. Institute CHI, November, 1998, Lisbon, Portugal) has shown that filtration steps (including nanofiltration) can substantially remove added TSE spikes in the fractionation of human plasma.

It is an object of the present invention to further develop and characterise the removal of abnormal infective prion proteins from protein-containing liquids, particularly those derived from human plasma, without unacceptable effects on the nature or biological activity of the proteins.

It is a further object of the present invention to provide a depth filter which can be a single use filter and may be disposed of having removed the abnormal prion proteins from the process stream.

The invention is based on the surprising discovery that filtration using a depth filter comprising particles and having a pore size less than six microns is surprisingly effective in removing abnormal infective prion proteins.

In particular, the invention provides a method for the removal of abnormal infective prion proteins associated with transmissable spongiform encephalopies (TSEs) from an aqueous liquid containing a natural product (especially a biologically active protein), which comprises passing the liquid through a depth filter formed of a matrix comprising solid particles of porous material and having a pore size providing a retention less than 6 μm. Typically the filter may be a single use disposable filter.

By the term "removal" is meant the actual physical removal of the abnormal infective prion protein from the liquid containing the desired protein. For practical purposes, the recovery of the desired protein in its original biological state should be substantially maintained at least to a level in excess of 50%, preferably 80%, more preferably 90%.

Removal of the abnormal infective prion protein may be achieved to an extent of at least $10^{2.5}$, $10^3$, preferably $10^4$, more particularly $10^5$.

The pore size of the filter matrix is preferably in the range 0.6 to 6 microns, particularly 0.6 to 1.5 microns. The pore size is defined in terms of the particle size of particles retained thereon. Typically particles of defined size such as microorganisms are used for calibration purposes.

The invention also relates to the treated liquid.

Of particular importance to the fractionation of blood plasma products, is the discovery that filtration may be effectively carried out under non-denaturing conditions for the biologically active protein, and under conditions which do not reduce the solubility of the product protein. In addition filtration with or without filter aid can be used to remove suspended solids.

The method may be carried out at a pH in the range 4-10, preferably 5-9, and especially 6-8.

The application of heat is unnecessary and the process can be conducted at substantially room temperature or below, in particular in the range −5 to +20° C.

Preferably, the liquid and the filter are free of cationic or anionic charged material which may contribute to the reduction of biological activity of the biologically active protein, and in particular may cause activation of sensitive blood coagulation factors. The process is in particular applicable to the treatment of whole blood or liquids containing albumin, immunoglobulins, Factor IX, thrombin, fibronectin, fibrinogen, Factor VIII and Factor II, VII, IX and X and other proteins derived from plasma. It is also applicable to the treatment of plasma, Factor XI, Factor XIII, haemoglobin, alpha-2-macroglobulin, haptoglobin, transferrin, apolipoprotein, mannan binding protein, protein C, protein S, caeruloplasmin, C-1-esterase inhibitor, inter-alpha-trysin inhibitor, Van Willebrand factor. Recombinant analogues of these may also be treated. In addition, the invention is applicable to the treatment of other natural products including foods, drinks, cosmetics etc. It is also applicable to other non-plasma animal-derived products, such as heparin and hormones.

The depth filter generally comprises a binder, such as cellulose, together with a solid porous particulate material such as Kieselguhr, perlite or diatomaceous earth.

The depth filter generally has a thickness in the region 1-10 mm, particularly 2-5 mm. The material used for the depth filter should have little or no effect on the desirable protein concerned.

Embodiments of the present invention will now be described by way of example only.

Methodology

1) Preparation of Hamster Scrapie Spike

Hamster adapted scrapie ($H_s$) agent (strain 263K) was prepared by homogenisation of infected brain tissue in phosphate buffered saline. The titre of the agent produced in this way is normally of the order of $10^7$-$10^9$ $LD_{50}$ units $ml^{-1}$ as assayed by the intracranial route in hamster. A stock of the hamster adapted scrapie strain agent (263K) is stored at or below −70 C.

A microsomal fraction derived from crude brain homogenate was used for all spiking experiments.

The microsomal fraction was prepared according to the method of Millson et al (Millson G C, Hunter G D and Kimberlin R H (1971); "An experimental examination of the scrapie agent in the cell membrane mixtures. The association of scrapie activity with membrane fractions", J. Comp Path. 81, 255-265). Crude brain homogenate prepared from 263K infected brains by Dounce homogenisation was pelleted at 10,000 g for 7 min to remove nuclei, unbroken cells and mitochondria. The microsomes remaining in the supernatant were then pelleted by centrifugation at 100,000 g for 90 min, followed by resuspension in PBS.

2) Calculation of Results

Clearance (C) and reduction (R) factors were calculated based on the end point dilution for samples after analysis by Western blotting. The end point dilution is calculated based on the first dilution at which no scrapie prion protein ($PrP^{sc}$) can be detected. The reciprocal of this dilution is then taken as the titre of agent, and thus all titres are expressed in arbitrary units. Based on the titre determined by end point dilution, the total amount of $PrP^{sc}$ in the sample is calculated based on the volume of the sample and taking into account any correction factors which need to be applied. Clearance factors are calculated relative to the theoretical input spike. Reduction factors are calculated relative to the level of $PrP^{sc}$ detected in the load sample.

Where no $PrP^{sc}$ is detected at the highest concentration of sample tested, then the reciprocal of the dilution is taken as 1, and clearance and reduction factors are expressed with a $\geq$ sign proceeding the logarithmic value.

3) Western Blot Assay for Scrapie Infectivity

The titre of the stock of 263K used in this study, as well as the titre present in all samples generated during the study was determined by a Western blot procedure. This procedure relies upon the difference in susceptibility of the infectious ($PrP^{sc}$) and non-infectious ($PrP^c$) to proteinase K digestion. Samples were treated with protease K to digest away any $PrP^c$, and run on a SDS polyacrylamide gel followed by blotting onto nitrocellulose. Any PrP remaining after protease digestion, corresponding to $PrP^{sc}$, was then detected using a PrP specific antibody. The relative level of scrapie in the samples compared to the stock was determined by serial dilution to end point (the point where no signal was detected) of all samples.

Further information is given in A. Bailey, "Strategies for the Validation of Biopharmaceutical Processes for the Removal of TSE's", Cambridge Healthtech Institute, Nov. 1998, Lisbon, Portugal.

Table 1 shows the efficiency of removal of spiked hamster scrapie prion proteins ($PrP^{sc}$) by various depth filters. Removal is expressed as clearance factor C (amount from innoculum/amount in filtrate) or as reduction factor R (amount in feedstock/amount in filtrate). The Seitz KS80 filter of pore size 0.6 to 1.5 microns according to the present invention is highly effective in removing the prion proteins. Other filters presented for comparison purposes having either a larger pore size or including cationic species are less effective.

EXAMPLES

Example 1

Treatment of Albumin According to the Invention

A model system was set up to replicate on an experimental scale the depth filtration of albumin in the conventional plasma fractionation process, employing different types of filter. The albumin-containing sample (fraction V) was spiked with hamster scrapie prion protein produced as described above and the concentration thereof was assessed by Western Blotting also as described herein.

The filter was a Seitz KS80 (trademark) pad cut to a 142 mm diameter disk of effective filtration area 128 cm². The filter was pretreated by passing ethanol and NaCl through for 35 minutes. The sample material was approximately 1 liter of resuspended fraction V at pH6.9 and 85.0 g/l concentration taken from the conventional plasma fractionation process and kept at +4° C.

The conventional process involves the batch filtration of 853 ml of sample. In this experiment, the same total volume of sample was passed through the filter, but only the final 100 ml was spiked with microsomal hamster scrapie. 100 ml of the sample starting material was spiked with 9.5 ml of the preparation of microsomal hamster (263k) scrapie and a sample of the spiked material was removed for analysis of the level of $PrP^{sc}$. The spiked material was passed through the filter at a flow rate of 6.4 ml/min and the filtrate collected for analysis of the level of $PrP^{sc}$. All samples were stored at or below −70° C. until analysis of the level of $PrP^{sc}$ was carried out. Before the samples were analysed by Western Blotting, any scrapie in the sample was concentrated by ultracentrifugation.

Table 1 shows that the removal assessed by clearance factor C and reduction factor R exceeds four log units (the detection limit) with no abnormal prion protein being detected in the filtrate. The filter is therefore most effective in removing the added spike of hamster scrapie prion protein.

Example 2

Albumin Treatment—Comparison

The fraction V albumin-containing sample was filtered with a different filter in a similar manner to Example 1.

The filter used was a Cuno (trademark) Delipid Del 1 mini cartridge of effective filtration area 27 $cm^2$. The filter was pretreated with ethanol and NaCl.

The sample material was fraction V at pH 6.9 and 85 g/l concentration taken after conventional filtration through a Seitz KS80 filter and held at +4° C.

In this case, only the final 50 ml were spiked with microsomal hamster scrapie. The spiked material was passed through the filter at a flow rate of 3.2 ml/min and the filtrate analysed for prion protein as before. The extent of clearance is shown in Table 1. Clearance and removal were only 2.8 and 2.3 logs respectively; abnormal prion protein being detected in the filtrate.

Example 3

IGG—Comparison

The procedure of Example 1 was repeated on IgG-containing supernatant I and III from conventional plasma fractionation.

The filter was a Millipore lifegard CP20 disk 47 mm in diameter providing an effective filtration area of 12.5 $cm^2$. The sample material was about 800 ml of supernatant I and III (prefiltration) from the conventional plasma fractionation procedure and held at +4° C. It contained about 12% ethanol and had a pH 5.1.

680 ml of sample was treated and the final 50 ml was spiked with microsomal hamster scrapie.

The extent of removal of prion proteins is given in Table 1. The clearance factor C was 3.0 logs and the removal R was less than 1 log; abnormal prion protein being detected in the filtrate.

Example 4

IGG—Invention

The general procedure of Example 1 was repeated on IgG-containing fraction II suspension from conventional plasma fractionation.

The filter was a Seitz K200 (trademark) of 142 mm diameter and effective filtration area 128 $cm^2$. The sample material was resuspended fraction II from conventional plasma fractionation held at +4° C.

600 ml of sample was passed through the filter and the final 100 ml was spiked with microsomal hamster scrapie. The extent of removal of the $PrP^{sc}$ was determined as before and the results are given in Table 1. The clearance C and removal R both showed no abnormal prion protein in the filtrate to the limit of detection (C≧3.4 and R≧2.8).

Thus, it can be seen from the Examples that greater than $10^4$ times removal of abnormal infective prion proteins can be achieved using a neutral filter having a pore size of less than 2 microns, and greater than $10^{2.5}$ times removal using a neutral filter of pore size 3.5 to 6.0 microns. These are the limits of detection. In other words no detectable abnormal prion protein was present in the filtrate.

Example 5

Fibre Filters—Comparison

Four filters formed of fibres were tested for prion removal in a manner similar to Example 1.

Whole blood was spiked with 3.8 $\log_{10}$ of hamster scrapie (Hs 263K) and the clearance C and removal R determined.

The results given in Table 2 shows that these fibre filters gave <1 log removal and were therefore ineffective for removing prion proteins.

TABLE 1

REMOVAL OF $PrP^{sc}$ BY DEPTH FILTRATION

| FILTER (PRODUCT) | COMPOSITION | RETENTION (μm) | C | R |
|---|---|---|---|---|
| Seitz, KS80 (Albumin) | Cellulose, Kieselguhr Perlite | 0.6-1.5 | ≧4.1 | ≧4.9 |
| Seitz, K200P (IgG) | Cellulose, Kieselguhr Perlite | 3.5-6.0 | ≧3.4 | ≧2.8 |
| Cuno, Delipid 1 (Albumin) | Cellulose, Kieselguhr Cation Resin | 0.6 | 2.8 | 2.3 |
| Millipore CP20 (IgG) | Borosilicate glass | 2.0 | 3.0 | <1* |

* Large drop in $PrP^{sc}$ measured after addition of inoculum to process feedstock.

TABLE 2

| FILTER (PRODUCT) | COMPOSITION | RETENTION (μm) | C | R |
|---|---|---|---|---|
| Baxter/Asahi Optiplus | Negatively charged polyester fibres | n/a | <1 | <1 |

TABLE 2-continued

| FILTER (PRODUCT) | COMPOSITION | RETENTION (μm) | C | R |
|---|---|---|---|---|
| R7456(RS2000) Fresenius whole blood filter compoflex T2916 | Melt blown woven-non-woven polyester fibre Non-ionic surface | n/a | <1 | <1 |
| Macopharma eucoflex LST-1 | Nonwoven non ionic surface polyester/ polypropylene mixture 4 layers polyester/22 layers polypropylene/ 1 layer polyester | 6-13 | <1 | <1 |
| Pall leukotrap BPF-4 | Non-woven polyester negatively charged | n/a | <1 | <1 | n/a - not available

The invention claimed is:

1. A method of removal of abnormal infective prion proteins associated with transmissible spongiform encephalopies (TSEs) from an aqueous liquid wherein the aqueous liquid contains a blood plasma product derived from plasma, which method consists essentially of passing the aqueous liquid containing the blood plasma product through a depth filter formed of a matrix comprising (a) a binder and (b) kieselguhr or perlite particles or mixtures thereof and having a pore size providing a retention less than 6 μm, and so removing abnormal infective prion proteins which may be present in the blood plasma product contained within the aqueous liquid such that the aqueous liquid is non-infective with respect to prion protein infectivity.

2. The method according to claim 1, wherein the binder is cellulose.

3. The method according to claim 1, carried out in the absence of cationic or anionic charged material.

4. The method according to claim 1 carried out at a pH in the range 4 to 10.

5. The method according to claim 1, wherein the pore size is in the range 0.6 to 6 microns.

6. The method according to claim 1, wherein the pore size is in the range 0.6 to 1.5 microns.

7. The method according to claim 1, wherein the depth filter has a thickness of 2 to 5 mm.

8. The method according to claim 1, wherein the plasma is human plasma.

9. The method according to claim 8, wherein the blood plasma product is selected from the group consisting of albumin, an immunoglobulin, Factor IX, thrombin, fibronectin, fibrinogen, Factor VIII, Factor II, Factor VII, Factor IX, and Factor X.

10. The method according to claim 1, wherein the aqueous liquid comprises a product selected from the group consisting of heparin and hormones.

11. The method according to claim 1, wherein the abnormal infective prion protein is associated with conditions selected from the group consisting of Creutzfeldt-Jakob Disease, variant Creutzfeldt-Jakob Disease, bovine spongiform encephalopy and scrapie.

12. The method according to claim 1, wherein the blood plasma product is selected from the group consisting of immunoglobulins and albumin.

13. The method of claim 1, wherein the filter is pretreated with ethanol.

14. The method of claim 1, wherein the depth filter has a permeability of 110 or 220 L/m$^2$/min.

15. The method of claim 1, wherein the depth filter is a single use filter.

16. The method of claim 1, wherein the aqueous liquid is a cell-free blood plasma product.

17. The method of claim 1, wherein the pore size is more than a pore size that is too small to allow passage of plasma proteins and the depth filter is a single use filter.

18. The method of claim 1, wherein the blood plasma product derived from plasma passes through the depth filter.

19. A method for the removal of abnormal infective prion proteins associated with a transmissible spongiform encephalopathy (TSE) from an aqueous blood plasma product, consisting essentially of passing the aqueous blood plasma product through a depth filter,
wherein the depth filter has a pore size of 6 μm or less and comprises a binder and solid particles of porous material selected from the group consisting of kieselguhr, perlite and mixtures thereof,
thereby removing abnormal infective prion proteins from the aqueous blood plasma product and rendering the aqueous blood plasma product non-infective with respect to prion protein infectivity.

20. The method of claim 19, wherein the abnormal infective prion proteins are associated with a TSE selected from the group consisting of bovine spongiform encephalopathy, Creutzfeldt-Jakob disease, variant Creutzfeldt-Jakob disease and scrapie.

21. The method of claim 19, wherein the blood plasma product is derived from human plasma.

22. The method of claim 19, wherein the blood plasma product is a plasma fraction.

23. The method of claim 19, wherein the blood plasma product is free of cationic or anionic charged material.

24. The method of claim 19, wherein the blood plasma product is a cell-free blood plasma product.

25. The method of claim 19, wherein the blood plasma product comprises a biologically active protein, heparin or hormones.

26. The method of claim 25, wherein the biologically active protein is selected from the group consisting of albumin, Factor II, Factor VII, Factor VIII, Factor IX, Factor X, fibrinogen, fibronectin, immunoglobulins and thrombin.

27. The method of claim 25, wherein the biologically active protein is selected from the group consisting of albumin and immunoglobulins.

28. The method of claim 25, wherein more than 90% of the biologically active protein is retained in the aqueous blood plasma product upon passing the aqueous blood plasma product through the depth filter.

29. The method of claim 19, wherein the depth filter is a neutral filter.

30. The method of claim 19, wherein the depth filter is a single-use filter.

31. The method of claim 19, wherein the depth filter is pretreated with ethanol.

32. The method of claim 19, wherein the depth filter has a pore size in the range of 0.6 to 6.0 microns.

33. The method of claim 19, wherein the depth filter has a pore size in the range of 3.5 to 6.0 microns.

34. The method of claim 19, wherein the depth filter has a pore size in the range of 0.6 to 1.5 microns.

35. The method of claim 19, wherein the depth filter has a thickness in the range of 2 to 5 mm.

36. The method of claim 19, wherein the depth filter has a permeability in the range of 110 to 220 L/m$^2$/min.

37. The method of claim 19, wherein the binder is cellulose.

38. The method of claim 19, wherein the solid particles of porous material comprise a mixture of kieselguhr and perlite particles.

39. The method of claim 19, wherein the method is carried out under non-denaturing conditions.

40. The method of claim 19, wherein the method is carried out at a pH in the range of 4 to 10.

41. The method of claim 19, wherein the method is carried out at a pH in the range of 6 to 8.

42. The method of claim 19, wherein the method is carried out at a temperature in the range of −5 to 20 degrees Celsius.

43. A method for the removal of abnormal infective prion proteins associated with a transmissible spongiform encephalopathy (TSE) from an aqueous blood plasma product, consisting essentially of passing the aqueous blood plasma product through a neutral depth filter,
wherein the depth filter has a pore size of 0.6 to 1.5 μm and comprises a cellulose binder and a mixture of kieselguhr and perlite particles,
thereby removing abnormal infective prion proteins from the aqueous blood plasma product and rendering the aqueous blood plasma product non-infective with respect to prion protein infectivity.

* * * * *